(12) United States Patent
Ghanouni et al.

(10) Patent No.: US 12,257,383 B2
(45) Date of Patent: Mar. 25, 2025

(54) ARTICLE FOR USE WITH AN APPARATUS FOR HEATING AN AEROSOL GENERATING AGENT

(71) Applicant: Nicoventures Trading Limited, London (GB)

(72) Inventors: Kaveh Ghanouni, London (GB); Richard Hepworth, London (GB); Walid Abi Aoun, London (GB); Karl Kaljura, London (GB); Thomas David Leah, London (GB); Shasa Harris, London (GB)

(73) Assignee: NICOVENTURES TRADING LIMITED, London (GB)

( * ) Notice: Subject to any disclaimer, the term of this patent is extended or adjusted under 35 U.S.C. 154(b) by 60 days.

(21) Appl. No.: 18/149,947

(22) Filed: Jan. 4, 2023

(65) Prior Publication Data
US 2023/0144274 A1    May 11, 2023

Related U.S. Application Data

(62) Division of application No. 16/492,653, filed as application No. PCT/EP2018/058195 on Mar. 29, 2018, now Pat. No. 11,571,527.

(30) Foreign Application Priority Data

Mar. 30, 2017 (GB) ...................... 1705152

(51) Int. Cl.
*A61K 31/282* (2006.01)
*A24B 3/14* (2006.01)
(Continued)

(52) U.S. Cl.
CPC .......... *A61M 15/0028* (2013.01); *A24B 3/14* (2013.01); *A24B 15/12* (2013.01); *A24B 15/16* (2013.01);
(Continued)

(58) Field of Classification Search
None
See application file for complete search history.

(56) References Cited

U.S. PATENT DOCUMENTS

| 4,714,082 A | 12/1987 | Banerjee et al. |
| 5,133,368 A | 7/1992 | Neumann et al. |

(Continued)

FOREIGN PATENT DOCUMENTS

| CA | 2864371 C | 8/2013 |
| CN | 103987286 A | 8/2014 |

(Continued)

OTHER PUBLICATIONS

Definition of kit, Merriam-Webster, [online], retrieved from the Internet, [retrieved Dec. 17, 2021], <URL: https://www.merriam-webster.com/dictionary/kit>. (Year: 2021).*

(Continued)

*Primary Examiner* — Dennis R Cordray
(74) *Attorney, Agent, or Firm* — WOMBLE BOND DICKINSON (US) LLP

(57) ABSTRACT

An article for use with an apparatus for heating aerosol generating agent to volatilize at least one component of the aerosol generating agent, the article including a support layer having a first surface, wherein at least a portion of the first surface is rough and an aerosol generating agent on the portion of the first surface that is rough.

9 Claims, 8 Drawing Sheets

(51) Int. Cl.

| | |
|---|---|
| *A24B 15/12* | (2006.01) |
| *A24B 15/16* | (2020.01) |
| *A24B 15/167* | (2020.01) |
| *A24B 15/24* | (2006.01) |
| *A24B 15/28* | (2006.01) |
| *A24D 1/20* | (2020.01) |
| *A24F 40/20* | (2020.01) |
| *A24F 40/46* | (2020.01) |
| *A24F 47/00* | (2020.01) |
| *A61K 45/06* | (2006.01) |
| *A61K 47/64* | (2017.01) |
| *A61M 15/00* | (2006.01) |
| *A61M 15/06* | (2006.01) |
| *C07F 15/00* | (2006.01) |

(52) U.S. Cl.
CPC ............ *A24B 15/167* (2016.11); *A24B 15/24* (2013.01); *A24B 15/28* (2013.01); *A24D 1/20* (2020.01); *A24F 40/20* (2020.01); *A24F 40/46* (2020.01); *A24F 47/00* (2013.01); *A61M 15/06* (2013.01); *A61K 31/282* (2013.01); *A61K 45/06* (2013.01); *A61K 47/643* (2017.08); *A61M 2205/0238* (2013.01); *C07F 15/0093* (2013.01)

(56) References Cited

U.S. PATENT DOCUMENTS

| | | | |
|---|---|---|---|
| 5,369,723 A | 11/1994 | Counts et al. | |
| 2004/0099279 A1* | 5/2004 | Chapman ............... | A24D 1/025 131/365 |
| 2008/0216828 A1 | 9/2008 | Wensley et al. | |
| 2009/0293888 A1 | 12/2009 | Williams et al. | |
| 2011/0290268 A1 | 12/2011 | Schennum | |
| 2012/0042885 A1 | 2/2012 | Stone et al. | |
| 2014/0373856 A1* | 12/2014 | Zuber ..................... | A24F 40/00 131/328 |
| 2016/0295922 A1* | 10/2016 | John ....................... | A24F 40/46 |
| 2016/0295926 A1 | 10/2016 | Zuber | |
| 2019/0098930 A1 | 4/2019 | Fallon et al. | |

FOREIGN PATENT DOCUMENTS

| | | |
|---|---|---|
| CN | 105744850 A | 7/2016 |
| CN | 105899095 A | 8/2016 |
| CN | 105939624 A | 9/2016 |
| CN | 106488714 A | 3/2017 |
| DK | 649987 | 12/1987 |
| JP | H07502188 A | 3/1995 |
| JP | 2014511675 A | 5/2014 |
| JP | 2015503336 A | 2/2015 |
| JP | 2016538842 A | 12/2016 |
| JP | 2019513349 A | 5/2019 |
| RU | 2085092 C1 | 7/1997 |
| RU | 2544158 C1 | 3/2015 |
| WO | 2010146693 A1 | 12/2010 |
| WO | 2013098409 A1 | 7/2013 |
| WO | 2015071682 A1 | 5/2015 |
| WO | 2015082648 A1 | 6/2015 |
| WO | 2015082653 A1 | 6/2015 |
| WO | 2017167932 A1 | 10/2017 |
| ZM | 6285 A1 | 1/1986 |

OTHER PUBLICATIONS

Intention to Grant received for European Patent Application No. 18717862.9, mailed on Sep. 21, 2022, 8 pages.
International Preliminary Report on Patentability received for PCT Patent Application No. PCT/EP2018/058195, mailed on Oct. 10, 2019, 11 pages.
International Search Report and Written Opinion received for PCT Patent Application No. PCT/EP2018/058195, mailed on Nov. 12, 2018, 17 Pages.
Invitation to Pay Additional Fees received for PCT Patent Application No. PCT/EP2018/058195, mailed on Jul. 18, 2018, 11 pages.
Office Action received for Chinese Patent Application No. 201880022566.0, mailed on Jul. 23, 2021, 9 pages.
Office Action received for Japanese Patent Application No. 2019-549558, mailed Nov. 24, 2020, 9 pages.
Office Action received for Korean Patent Application No. 10-2019-7028182, mailed on Nov. 1, 2021, 9 pages.
Office Action received for Russian Patent Application No. 2019130437, mailed on Apr. 28, 2020, 18 pages.
Merriam-Webster , "Definition of adhere", retrieved from the Internet <URL:https://www.merriam-webster.com/dictionary/adhere>, 2022.
Merriam-Webster , "Definition of foil", retrieved from the Internet <URL: https://www.merriam-webster.com/dictionary/foil>, 2021.
Merriam-Webster , "Definition of kit", retrieved from the Internet <URL: https://www.merriam-webster.com/dictionary/kit>, 2021.
Notice of Reasons for Rejection received for Japanese Patent Application No. 2021-150188, mailed on Feb. 21, 2023, 5 pages (2 pages of English Translation and 3 pages of Official Copy).

\* cited by examiner

ARTICLE FOR USE WITH AN APPARATUS FOR HEATING AN AEROSOL GENERATING AGENT

PRIORITY CLAIM

The present application is a Divisional Application of U.S. application Ser. No. 16/492,652, filed Sep. 10, 2019, which is a National Phase entry of PCT Application No. PCT/EP2018/058195, filed Mar. 29, 2018, which claims priority from GB Patent Application No. 1705152.5, filed Mar. 30, 2017, which are all hereby fully incorporated herein by reference.

TECHNICAL FIELD

The present disclosure relates to an article for use with an apparatus for heating aerosol generating agent.

BACKGROUND

Smoking articles such as cigarettes, cigars and the like burn tobacco during use to create tobacco smoke. Attempts have been made to provide alternatives to these smoking articles by creating products that release compounds without actually combusting and hence which do not create smoke or an aerosol as a result of degradation of, for example, tobacco by combustion or the process of burning. Examples of such products are so-called heat-not-burn products, tobacco heating products or tobacco heating devices, which release compounds, which may form an aerosol, by heating, but not burning, aerosol generating material. The aerosol generating material may be for example tobacco or other non-tobacco products, which may or may not contain nicotine.

SUMMARY

In accordance with some embodiments described herein, there is provided an article for use with an apparatus for heating aerosol generating agent to volatilize at least one component of the aerosol generating agent, the article comprising a support layer having a first surface, wherein at least a portion of the first surface is rough; and an aerosol generating agent on the portion of the first surface that is rough. Providing the aerosol generating agent on the portion of the first surface that is rough, heat transfer from a heater to the article will be improved.

In an exemplary embodiment, the portion of the first surface that is rough comprises a plurality of protuberances.

In an exemplary embodiment, the portion of the first surface is embossed. Embossing the first surface is an efficient and easily repeatable way to obtain the rough surface.

In accordance with some embodiments described herein, there is provided an article for use with an apparatus for heating aerosol generating agent to volatilize at least one component of the aerosol generating agent, the article comprising a first substrate of paper having a first inner surface; and an aerosol generating agent on at least a portion of the first inner surface of the first sheet.

In accordance with some embodiments described herein, there is provided a system comprising an apparatus for heating aerosol generating agent to volatilize at least one component of the aerosol generating agent; and an article for use with the apparatus for heating aerosol generating agent to volatilize at least one component of the aerosol generating agent, the article comprising a support layer having a first surface, wherein at least a portion of the first surface is rough; and an aerosol generating agent on the portion of the first surface that is rough.

In accordance with some embodiments described herein, there is provided a kit comprising an apparatus for heating aerosol generating agent to volatilize at least one component of the aerosol generating agent; and an article for use with the apparatus for heating aerosol generating agent to volatilize at least one component of the aerosol generating agent, the article comprising a support layer having a first surface, wherein at least a portion of the first surface is rough; and an aerosol generating agent on the portion of the first surface that is rough.

In accordance with some embodiments described herein, there is provided a method of manufacturing a smoking article for use with an apparatus for heating aerosol generating agent to volatilize at least one component of the aerosol generating agent, the method comprising providing a support layer having a first surface, wherein at least a portion of the first surface is rough; and providing an aerosol generating agent on the portion of the first surface that is rough.

BRIEF DESCRIPTION OF THE DRAWINGS

Embodiments of the disclosure will now be described, by way of example only, with reference to the accompanying drawings, in which.

DETAILED DESCRIPTION

As used herein, the term "aerosol generating agent" includes agents that provide volatilized components upon heating. "Aerosol generating agent" includes any tobacco-containing material and may, for example, include one or more of tobacco, tobacco derivatives including tobacco extracts, expanded tobacco, reconstituted tobacco or tobacco substitutes. "Aerosol generating agent" may also include other, non-tobacco, products, including for example flavorants, which, depending on the product, may or may not contain nicotine, filler materials such as chalk and/or sorbent materials, glycerol, propylene glycol or triacetin. The aerosol generating agent may also include a binding material, for example, sodium alginate. The aerosol generating agent may include tobacco particles or leaves in solid form within the agent. In one example the aerosol generating agent is an aerosol forming gel. The aerosol generating gel may be a solid, jelly like material. The aerosol generating gel may be a newtonian or non-newtonian gel. In one example the gel is a thermoplastic gel. In one example, the aerosol generating gel has a viscosity of between 0.1 and 100 $Ns/m^2$.

Figure 1:
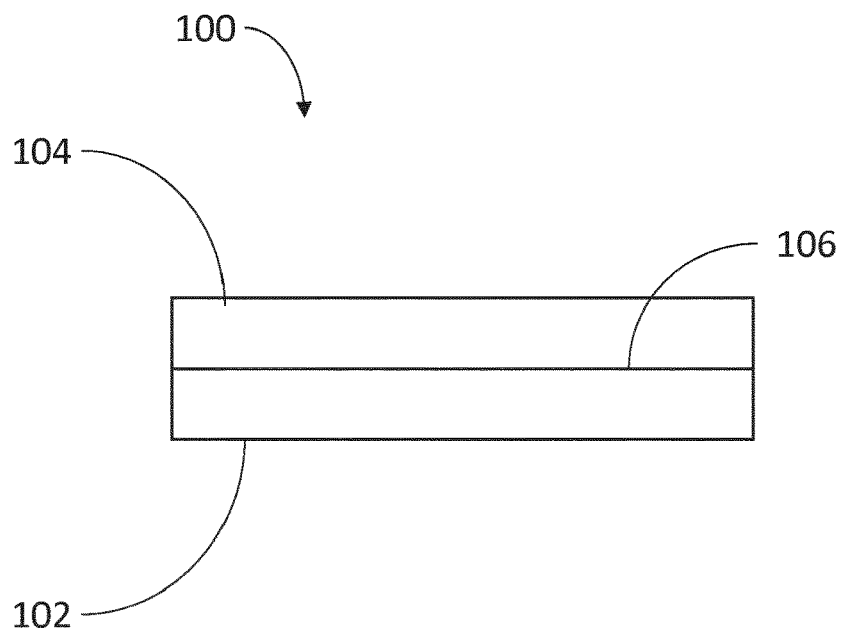
FIG. 1 shows a schematic side view of an article for use with an apparatus for heating aerosol generating agent to volatilize at least one component of the aerosol generating agent.
Figure 2:
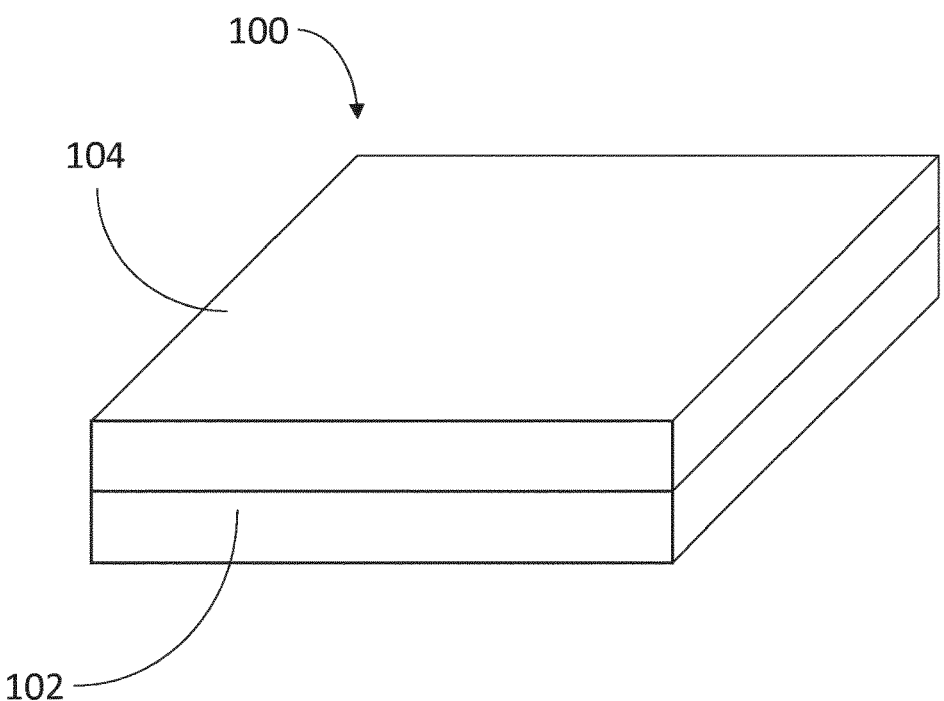
FIG. 2 shows a schematic perspective view of the article of FIG. 1.

Referring to FIGS. 1 to 2, there is shown an article 100 for use with an apparatus for heating aerosol generating agent to volatilize at least one component of the aerosol generating agent. The article 100 includes a support layer 102 and a layer of aerosol generating agent 104. The aerosol generating agent 104 is located on a first surface 106 of the support layer 102. The aerosol generating agent 104 forms a layer of material on the support layer 102 as shown in FIGS. 1 and 2, for example the layer of aerosol generating agent 104 is bonded to the support layer 102.

In the examples of the articles 100 shown in FIGS. 1 to 6, the support layer 102 has a substantially smooth first surface 106 on which the aerosol generating agent 104 is located. An example of a support layer 102 which has a smooth surface is aluminum foil.

Figure 3:
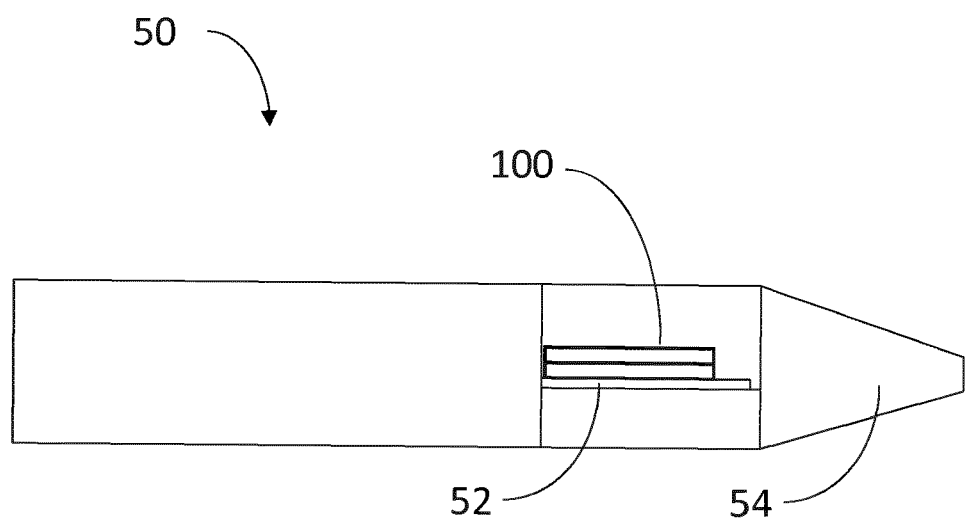
FIG. 3 shows a schematic perspective view of the first example of an apparatus for heating an aerosol generating material.

The article 100 is designed to be used with an apparatus for heating aerosol generating agent to volatilize at least one component of the aerosol generating agent, such as a so-called tobacco heating product, which includes a heater. An example of a heating apparatus is shown in FIG. 3. In one example, the apparatus 50 comprises a substantially flat heating surface 52 upon which, in use, the article 100 is placed such that the support layer 102 lies on the heating surface. In other examples, the heater may take the form of a cylindrical heater or a blade heater. In other example, the apparatus may comprise a heater to heat air which will subsequently pass over the surface of the aerosol generating agent to heat it. The heater may comprise a resistive heater, in another example, the heater may be an inductive heater and the article may be placed on a susceptor within the apparatus. In the example of the induction heating, the support layer 102 may be formed of a magnetic material and act as an additional susceptor so that an eddy current is generated when the support layer 102 is subjected to a varying magnetic field. The apparatus 50 is configured to heat the article 100 to volatilize at least one component of the aerosol generating agent. In the example of FIG. 3, the apparatus 50 includes a mouthpiece 54 through which the volatilized components may flow. However, in other examples, the apparatus does not include the mouthpiece 54.

In the example of the aerosol forming agent 104 comprising an aerosol forming gel, the aerosol forming gel 104 may be formed by mixing a concentrated tobacco extract with water in a high shear mixer with a binding agent, such as sodium alginate, to form a paste or slurry. An aerosol generating material, such as glycerol, is added and the paste is wet cast on as a thin film on a support layer 102, such as aluminum or paper. The thin film is then dried by applying heat to remove excess water from the film. In the drying phase, the articles 100 may be subject to a temperature of approximately 60 to 100 degrees Celsius for approximately 20 minutes to 5 hours. Depending on the chemicals used in the formulation of the thin films, the thin films exhibit a sticky surface that makes handling them in a commercial environment problematic. The thin films may also exhibit poor adhesion to the support layer 102 on which they have been cast, which may lead to problems during the drying phase and also when the article 100 is heated in use in the aerosol generating apparatus, which will be described in more detail below.

In one example, the aerosol forming agent 104 has a thickness of between 100 µm and 350 µm.

It has been observed that upon heating of the article, the aerosol generating agent 104 tends to become delaminated from the support layer 102. In addition, when the article 100 is placed on a heating surface 52 of the apparatus, the support layer 102 tends to curl, which results in a separation between the support layer 102 and the heating surface 52. The consequence of both of these examples is poor heat transfer from the heating surface 52 to the aerosol generating agent 104, which results in a poor aerosol delivery.

Figure 4A:
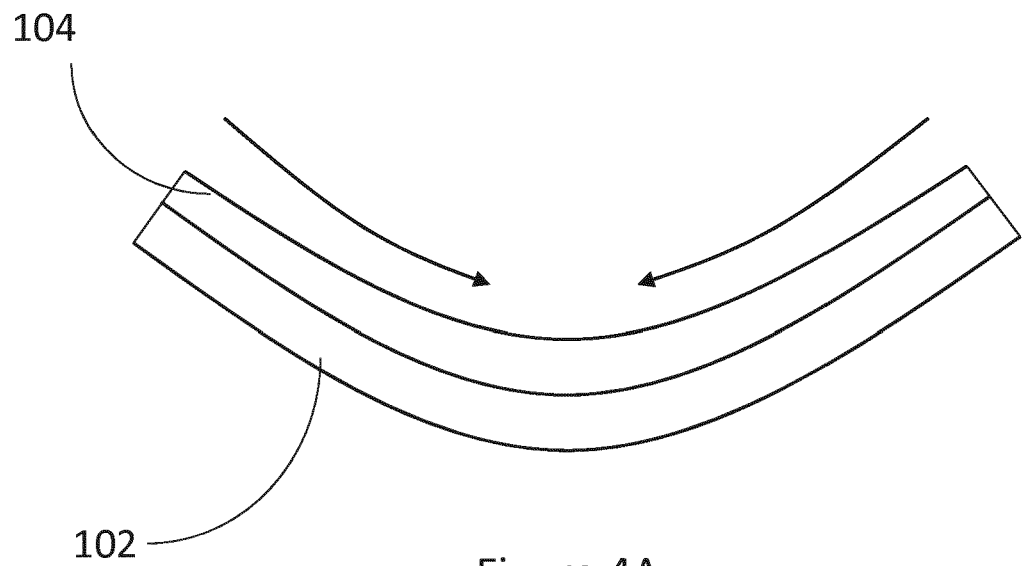
FIGS. 4A and 4B show an example of delamination between an aerosol forming agent and a substrate.
Figure 4B:
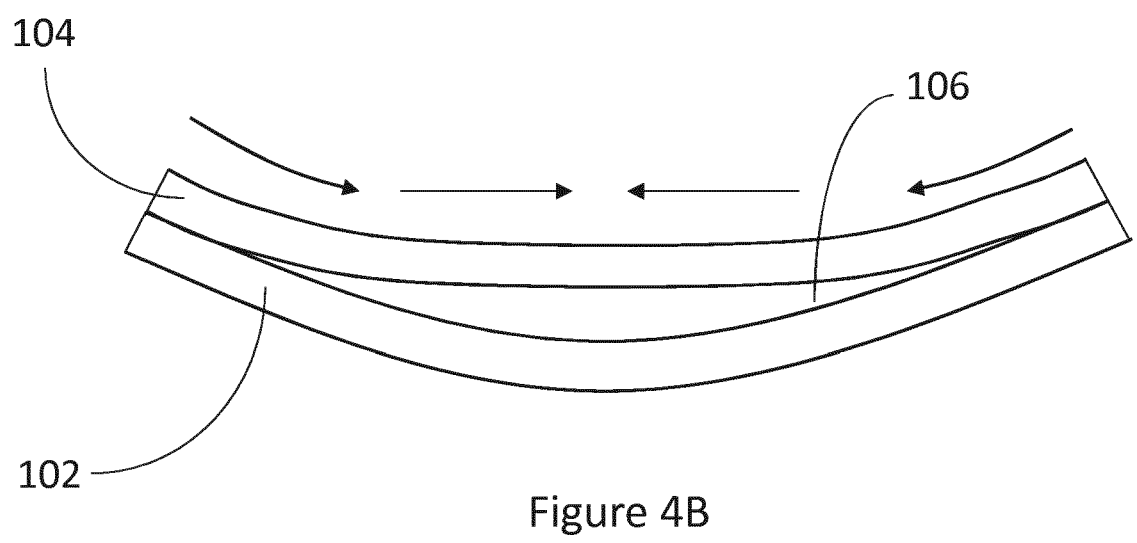

A first mechanism for delamination between the aerosol generating agent 104 and the support layer 102 is shown in FIGS. 4A and 4B. FIG. 4A shows an example of the article 100 during heating. The heating process causes water and or other components within the aerosol generating agent 104 to evaporate causing the agent to contract as shown by the arrows in FIG. 3A. The support layer 102 may be formed from a solid material, such as aluminum or paper and thus would not contract upon heating. As there is some adhesion between the aerosol generating material 104 and the support layer 102, the differential contraction between the aerosol generating agent layer 104 and the support layer 102 causes the article 100 to curl as shown in FIG. 3A. The self-weight of the support layer 102 causes the support layer 102 to resist the contraction of the aerosol generating agent 104. As the aerosol generating agent 104 continues to contract, the central part of the aerosol generating agent 104 may separate from the support layer 102 resulting in delamination of the aerosol generating agent 104 and the support layer 102. The degree of curling versus delamination depends on the level of adhesion between the aerosol generating agent 104 and the support layer 102, the stiffness of the support layer 102 and the stiffness of the aerosol forming agent 104.

Figure 5:
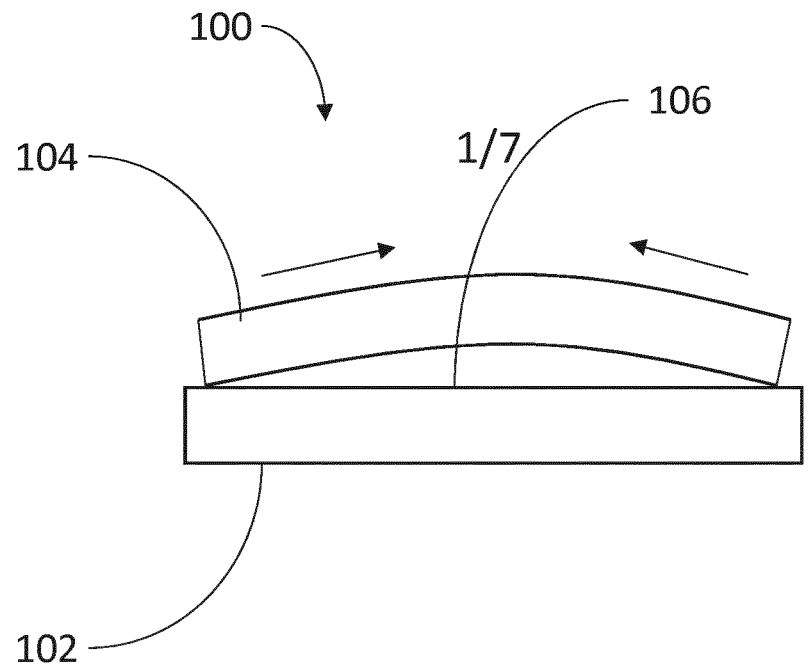
FIG. 5 shows a further example of delamination between an aerosol forming agent and a substrate.

A second mechanism for delamination between the aerosol generating agent 104 and the support layer 102 is shown in FIG. 5. FIG. 5 shows an example of the article 100 during heating. The heating process causes water and or other components within the aerosol generating agent 104 to evaporate. If the support layer 102 is placed on a heating surface 52 of an apparatus, then the surface of the aerosol generating agent 104 that is proximate to the first surface 106 of the support layer 102 (and hence the heating surface) will be heated faster compared with the surface of the aerosol forming agent 104 that is further from the heating surface 52. As a result, the surface of the aerosol generating agent 104 that is proximate to the first surface 106 of the support layer 102 will lose more water compared with the surface of the aerosol forming agent that is further from the heating surface and therefore will contract more as shown in FIG. 5.

Figure 6:
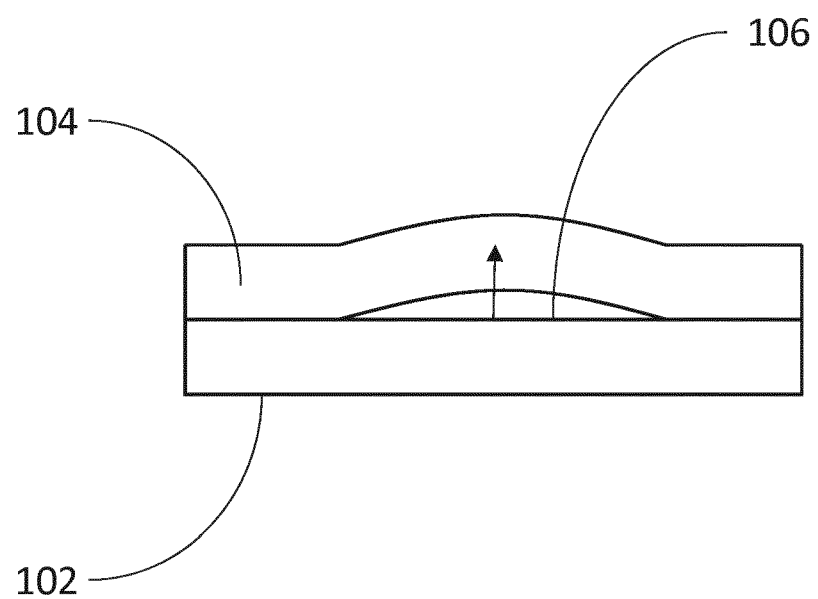
FIG. 6 shows a further example of delamination between an aerosol forming agent and a substrate.

A third mechanism for delamination between the aerosol generating agent 104 and the support layer 102 is shown in FIG. 6. As the aerosol generating agent 104 is heated, at least one component of the aerosol generating agent 104 is volatilized. If there is not a flow path between the volatilized component and the outer surface of the aerosol generating agent 104, then a build-up of volatilized components will act to separate the aerosol generating agent 104 from the support layer 102. There may also be air bubbles that get trapped in the aerosol generating agent 104 during the drying process that will expand upon heating and act to cause a delamination between the aerosol generating agent 104 and the support layer 102.

There is a need to improve heat transfer between a heater of the apparatus 50 and the article 100, which will improve the generation of volatilized components. Surprisingly, it was found that improving the adhesion sufficiently improves heat transfer for aerosol generating agents and results in a more efficient aerosol generating. One way of improving heat transfer is to improve adhesion between the aerosol generating agent 104 and the support layer 102 to reduce the delamination between the aerosol generating agent 104 and the support layer 102. One option for improving the adhesion between the aerosol generating agent 104 and the support layer 102 would be through the use of chemical additives to the aerosol generating agent 104 and the support layer 102. Powdered additives may be used to reduce the stickiness of the aerosol generating agent 104 to improve the handling of the agent. However, the use of additives has a number of drawbacks because components from the additives may be volatilized upon heating and be inhaled by a user, which may be undesirable. Further, the use of additives will increase the costs of creating the article 100.

Figure 7A:
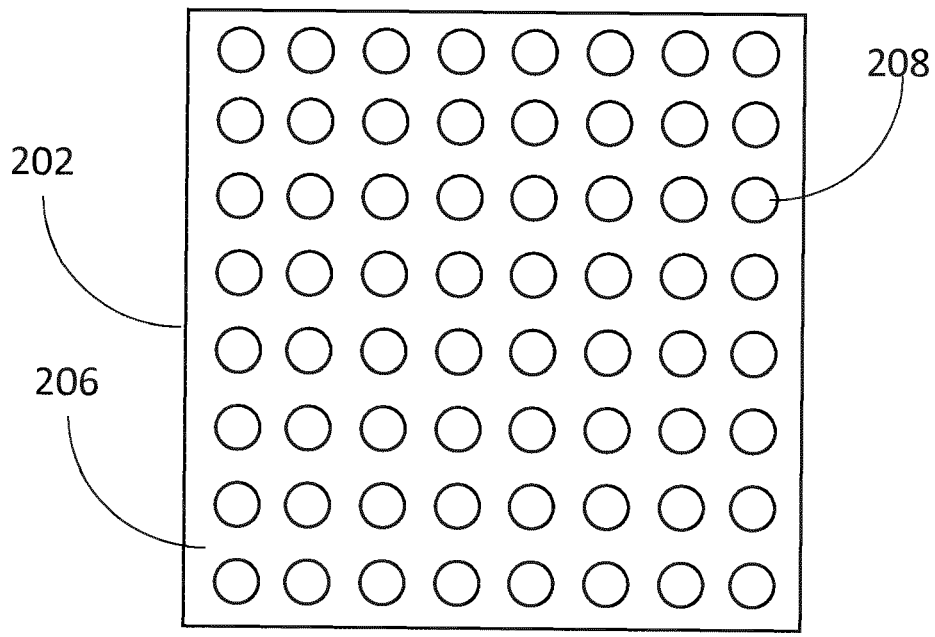
FIGS. 7A and 7B shows a schematic plan and perspective view of the first example of support layer with a rough first surface for receiving an aerosol generating agent.
Figure 7B:
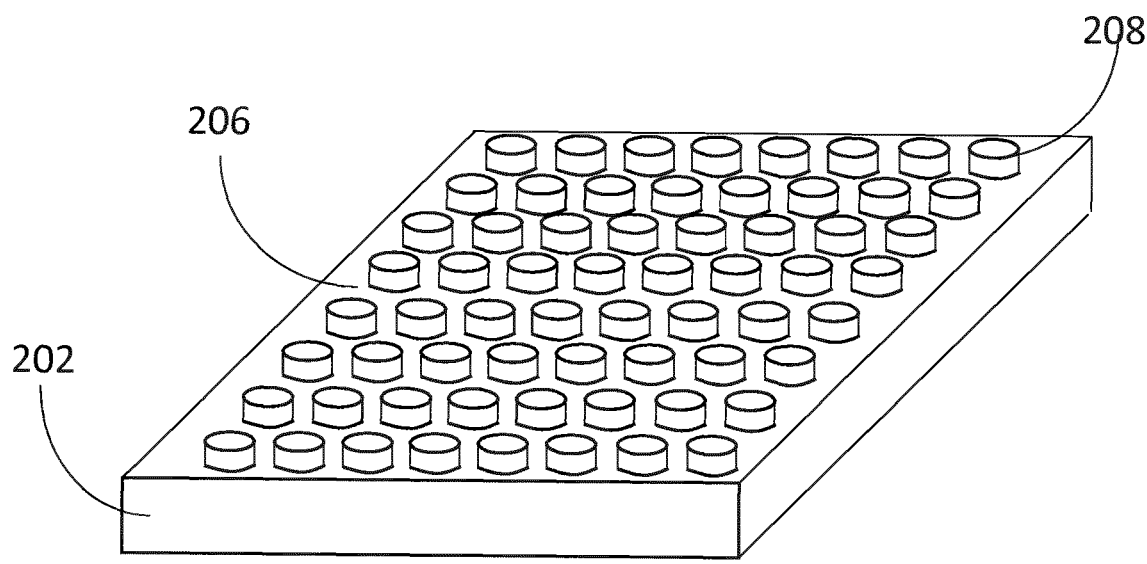

FIGS. 7A and 7B show an example of a support layer 202 in the form of a substrate having a first surface 206, wherein at least a portion of the first surface 206 is rough to provide an uneven or irregular surface. The first surface 206 is sufficiently rough to prevent or inhibit the delamination of the aerosol generating agent 204 from the first surface 206 of the support layer 202.

In one example, the first surface 206 is made rough by making a number of holes in the support layer 202. The holes may be made by penetrating the first surface 206 with a pin or series of pins.

The support layer 202 may be formed of any material suitable for receiving and holding the aerosol generating agent 204. In one example, the support layer 202 is formed from a heat conducting material, for example a metal such as aluminum. The support layer 202 may be, for example a metal foil such as aluminum foil.

In the example of the support layer 202 being formed of aluminum, the aluminum can have a thickness of between 5 µm to 25 µm. The aluminum thickness may be 7 µm, 10 µm or 20 µm, such as 6 µm to 8 µm.

In other examples, the support layer 202 is formed from a paper material, such as tipping paper, porous plug wrap, cigarette paper or tea bag paper. The paper may be a porous paper. When an aerosol generating gel is used as the aerosol generating agent, the gel may flow into the pores of the porous paper to improve adhesion. In the example of the support layer being formed from a paper material, the paper can have a weight of between 20 gsm and 100 gsm.

The aerosol forming agent 204 (not shown) will be located on the first surface 206 of the support layer 202. In the example shown in FIGS. 7A and 7B, the first surface 206 is rough due to the fact that there is a plurality of protuberances 208. Protuberances 208 are elements that protrude from the first surface 206 of the support layer 202. In the example shown in FIGS. 7A and 7B, the protuberances take the form of cylinders, however, any shape that projects from the first surface 206 of the support layer 202 may be used, such as cubes, pyramids and irregular shapes. It is not necessary for the protuberances 208 to be formed of the same shape. The protuberance 208 in FIGS. 7A and 7B are shown as covering most of the first surface 206 of the support layer 202, but in other example, the protuberances 208 only cover part of the first surface 206 of the support layer 202. In one example protuberances 208 may be formed by adding additional material or removing some material from the first surface 206 of the support later.

In one example the protuberances have a height of between 0.1 mm and 0.2 mm and a width of between 0.2 mm and 0.4 mm, such as a height of 0.15 mm and a width of 0.3 mm.

In one example, the first surface 206 of the support layer 202 is embossed to create the surface roughness. The support layer 202 may be embossed by stamping the support layer 202 with a mould to cause the first surface 206 of support layer 202 to have a three-dimensional or raised effect on selected areas. In some examples, the embossing procedure requires the use of two dies: one that is raised and one that is recessed. The dies fit into each other so that when the support layer 202 is pressed between them, the raised die forces the support layer 202 into the recessed die and creates the embossed surface.

The protuberances 208 may also be formed by embossing. Embossing the first surface 206 of the support layer 202 is a simple and repeatable way of creating a rough surface. The first surface 202 may be made rough by including one or more ridges, folds, indents, raised sections, holes.

The first surface 206 may be embossed using various patterns, such as one or more of spirals, lines; squares; circles; and/or rectangles.

Figure 7C:
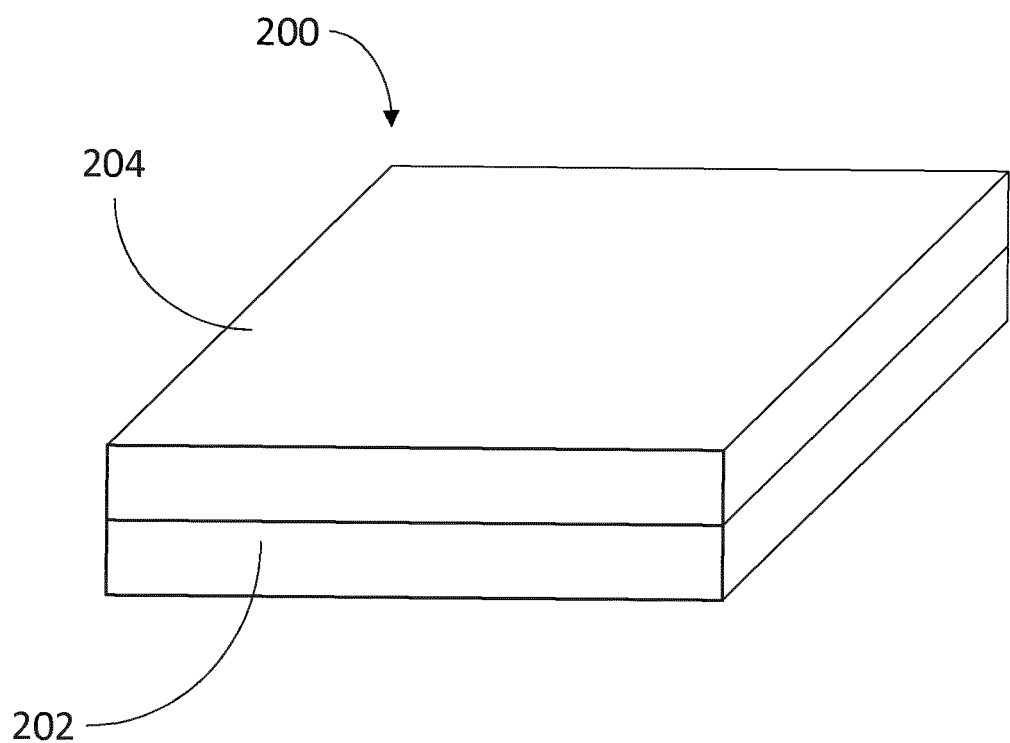
FIG. 7C shows a schematic perspective view of a first example of article for use with an apparatus for heating aerosol generating agent to volatilize at least one component of the aerosol generating agent.

The rough first surface 206 of the support layer 202, as shown in FIGS. 7A and 7B, acts to increase the contact surface area between the aerosol generating agent 204 and the support layer 202. An example of article 200 formed from the support layer 202 with a rough first surface 206 and aerosol generating agent 204 is shown in FIG. 7C. The increased surface area will increase the adhesion between the aerosol forming agent 204 and the support layer 202, and hence reduce the effects of the first two separation mechanisms described above. In relation to the first mechanism, the increased adhesion means that as the aerosol generating agent 204 contracts, it will be less likely to separate from the support layer 202. In relation to the second mechanism, the aerosol forming agent 204 is less likely to separate from the inner surface of the heat conducting layer because it will have a stronger adhesion to the inner surface. As the adhesion is increased, the aerosol forming agent 204 is less likely to delaminate from the support layer 202 and therefore when the article 200 is heated by a heating apparatus, more aerosol generating agent 204 will be heated.

The article 200 may be manufacturing by providing a support layer 202 having a first surface 206, wherein at least a portion of the first surface 206 is rough; and providing an aerosol generating agent 204 on the portion of the first surface 206 that is rough. As described above, the first surface 206 may be made rough by one or more of embossing the first surface 206, providing protuberances 208, or other means of roughening the surface.

Figure 8:
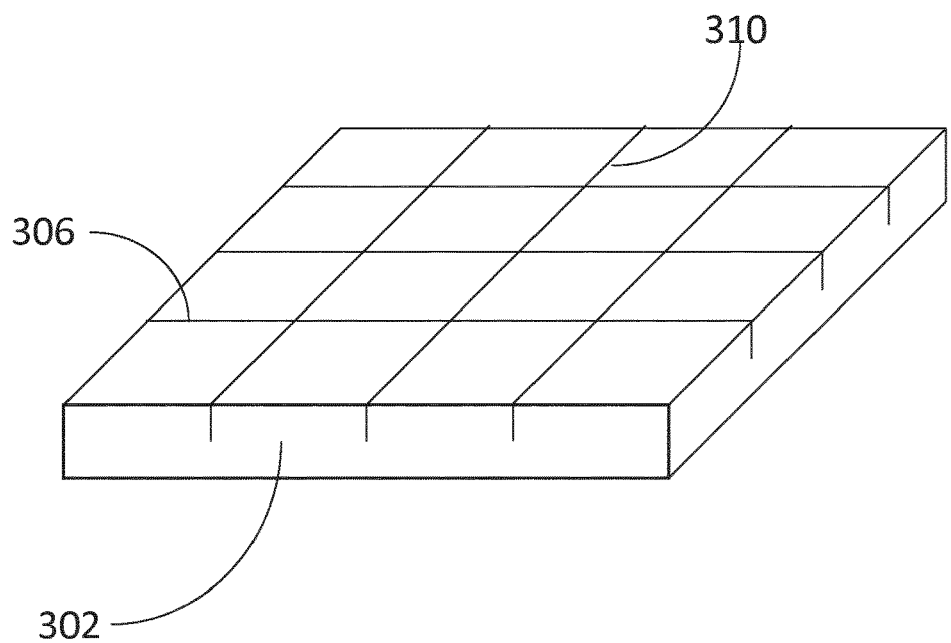
FIG. 8 shows a schematic perspective view of a support layer of the article with score lines.

In the further example shown in FIG. 8, the first surface 306 of the support layer 302 is made rough by having one or more score lines 310 formed in the first surface 306. The score lines may be formed by known processes such as running a cutting element over the first surface 306 of the support layer 306 to provide one or more cuts or indents in the first surface 306 of the support layer 302.

FIG. 8 shows the support layer 302 with six score lines 310 applied to the first surface 306, however, in some examples there are fewer score lines and in other examples there are more than six score lines 310 applied to the first surface 306. As with the protuberances 208 shown in FIG. 7B, score lines 310 perform the function of adding a surface roughness to the first surface of the support layer 310, which increases the adhesion between the aerosol generating agent 304 and the support layer 302. In one example, the surface roughness of the first surface 306 of the support layer 302 is provided by the score lines 310. In other examples, the surface roughness of the first surface 306 of the support layer is provided by a combination of one or more of the protuberances 208, embossment and the score lines 310.

Figure 9:
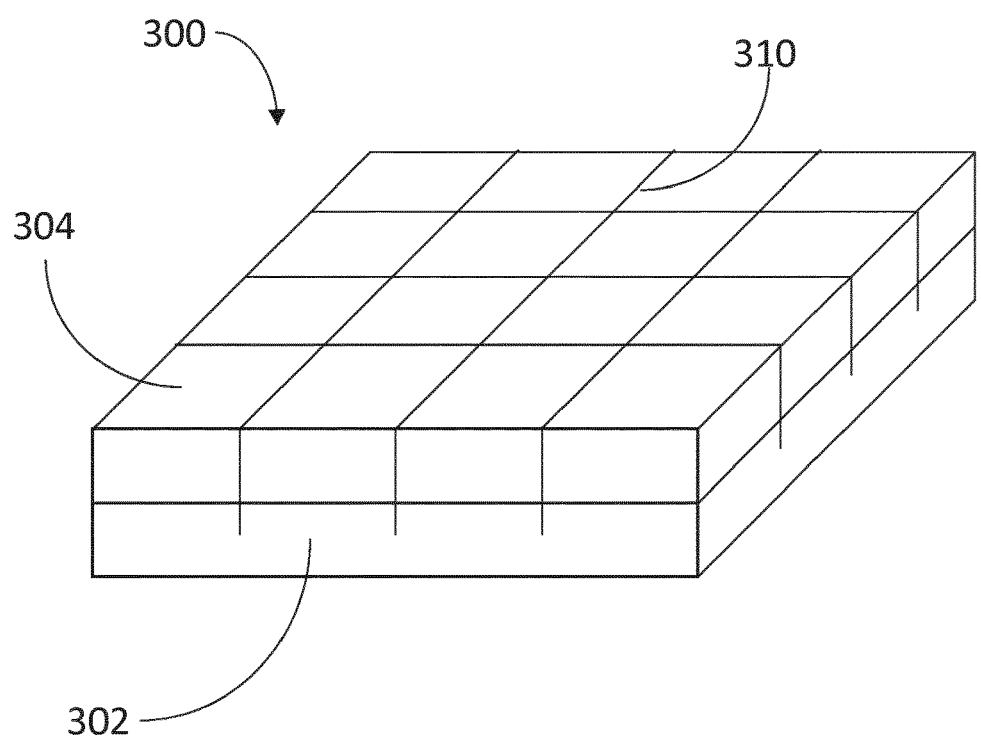
FIG. 9 shows a schematic perspective view of a second example of an article for use with an apparatus for heating aerosol generating agent to volatilize at least one component of the aerosol generating agent.

As shown in FIG. 9, the score lines 310 may also be applied to the aerosol generating agent 304. Applying score lines 310 to the aerosol generating agent 304 results in the aerosol generating agent 304 being pooled into one or more separate sections delineated by the score lines 310. Separating the aerosol generating agent 304 into separate sections provides more flow paths for any volatilized components and the outer surface of the aerosol generating agent 304. Therefore, the third mechanism of delamination between the aerosol generating agent 304 and the support layer 302 described above is less likely to occur. Further, separating the aerosol generating agent 304 into one or more separate sections helps reduce the curling effect described above.

Aerosol generating agents 104, 204, 304 may be formed from different tobacco extracts, such as Burley, Virgina and Oriental. Aerosol generating agents 204, 304 formed from different tobacco extracts may have different properties, for example, agents formed from Burley tobacco is more brittle, whereas agents formed from Virginia and Oriental is more pliable. Providing a first surface 306 of a support later 302, where at least a portion of the first surface is rough provides the best results when an aerosol generating agent 304 formed from an oriental tobacco is used.

T-Peel tests were carried out on a selection of samples. A T-Peel test involves testing the peel strength between the aerosol generating agent 304 and the support layer 302. Result of the T-Peel Test are shown below:

| Agent type | Support Layer Thickness | Layer Unembossed | Embossed |
|---|---|---|---|
| Burley | 20 μm | 4.5 +/− 0.8N/mm | 6.4 +/− 0.6N/mm |
| Oriental | 10 μm | 2.3 +/− 0.3N/mm | 3.9 +/− 0.8N/mm |

In a yet further example, the support layer 402 may be formed from paper, such as tipping paper, porous plug wrap, cigarette paper or tea bag paper. As paper is a fibrous substrate, the surface of the paper will be irregular. When an aerosol generating agent is applied to the surface of the paper, the aerosol generating agent will contact the irregular surface and will adhere to a first surface of the paper substrate. The inventors found that surprisingly, the aerosol generating agent 404 did not weaken the thin paper support and upon casting, the paper retained its integrity and after drying, the thin film adhered strongly to the paper substrate. This makes an article 400 that uses a paper substrate as the support layer an ideal system for use in a heating apparatus because the paper is thin enough not to act as a significant "insulation layer" so heat transfer is acceptable.

In one example, the apparatus for heating aerosol generating agent to volatilize at least one component of the aerosol generating agent may be sold in a kit, together with the article according to any of the examples described above.

The examples above show an aerosol generating agent on a first surface of a support layer, however, in other examples the support layer may include a first surface and a second surface, wherein at least a portion of the first surface is rough; and at least a portion of the second surface is rough. The second surface may be arranged on the opposite side of the support layer to the first surface. An aerosol generating agent is applied to the portion of the first surface that is rough and to the portion of the second surface that is rough. This arrangement enables more aerosol generating agent to be held by the support layer. Alternatively, the article may comprise a second support layer, such that the aerosol generating agent is located in between the first and second support layers. As with the first support layer the second support layer may comprise a first and/or second surface that are rough.

Figure 10:
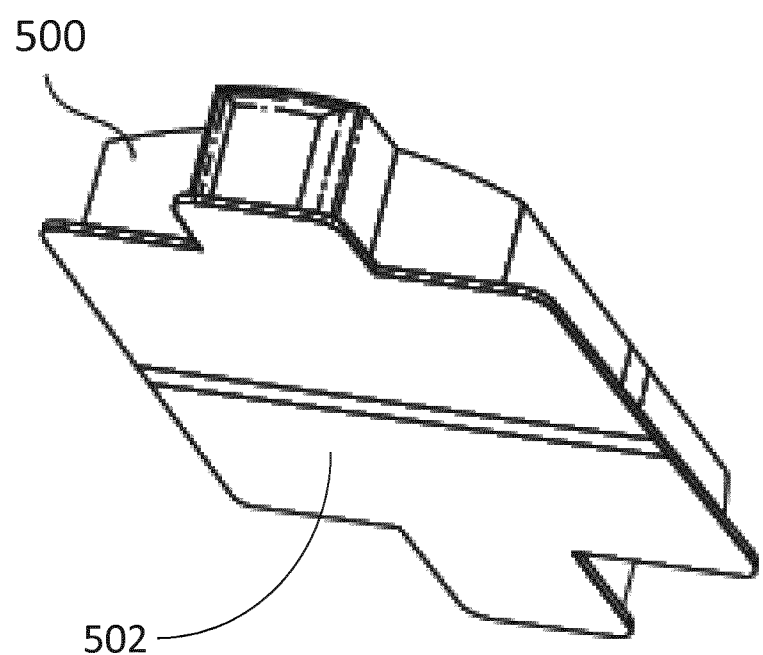
FIG. 10 shows a schematic view of an article for use with an apparatus for heating aerosol generating agent to volatilize at least one component of the aerosol generating agent.

FIG. 10 shows an example of an article according to any of the example above, wherein the article 500 is in the form of a cartridge that can be inserted into the apparatus 50 for heating aerosol generating agent to volatilize at least one component of the aerosol generating agent. The article 500 includes a support layer having a first surface (not shown) wherein at least a portion of the first surface is rough. An aerosol generating agent is be applied to the portion of the first surface that is rough.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc, other than those specifically described herein. In addition, this disclosure may include other inventions not presently claimed, but which may be claimed in future.

The invention claimed is:

1. An article for use with an apparatus for heating an aerosol generating agent to volatilize at least one component of the aerosol generating agent, the article comprising:
   a first substrate of paper having a first surface; and
   the aerosol generating agent on at least a portion of the first surface of the first substrate of paper;
   wherein the aerosol generating agent comprises an aerosol generating gel.

2. The article according to claim 1, wherein the first substrate of paper is selected from the group consisting of:
   tipping paper;
   porous plug wrap;
   cigarette paper; and
   tea bag paper.

3. The article according to claim 1, wherein the first substrate of paper has a mass per unit area of from about 20 gsm to about 100 gsm.

4. The article according to claim 1, wherein the first substrate of paper comprises a porous paper.

5. The article according to claim 1 wherein the aerosol generating agent is adhered to the portion of the first surface of the first substrate of paper.

6. The article according to claim 1, wherein the aerosol generating agent comprises one or more tobacco extracts selected from the group consisting of:

Burley;
Virginia; and
Oriental.

7. The article according to claim 1, wherein the aerosol generating agent has a thickness of from about 100 microns to about 350 microns on the portion of the first substrate of the first substrate of paper.

8. A system comprising:
an apparatus for heating aerosol generating agent to volatilize at least one component of the aerosol generating agent; and
the article of claim 1.

9. A kit comprising:
an apparatus for heating aerosol generating agent to volatilize at least one component of the aerosol generating agent; and
the article of claim 1.

\* \* \* \* \*